(12) United States Patent
Bauer et al.

(10) Patent No.: US 10,398,390 B2
(45) Date of Patent: Sep. 3, 2019

(54) TOMOGRAPHY FOR LARGE VOLUME 3D SCANS

(71) Applicants: Sebastian Bauer, Erlangen (DE);
Patrick Kugler, Erlangen (DE);
Günter Lauritsch, Nürnberg (DE);
Andreas Maier, Erlangen (DE); Daniel Stromer, Höchstadt (DE)

(72) Inventors: Sebastian Bauer, Erlangen (DE);
Patrick Kugler, Erlangen (DE);
Günter Lauritsch, Nürnberg (DE);
Andreas Maier, Erlangen (DE); Daniel Stromer, Höchstadt (DE)

(73) Assignee: Siemens Healthcare GmbH, Erlangen (DE)

( * ) Notice: Subject to any disclaimer, the term of this patent is extended or adjusted under 35 U.S.C. 154(b) by 205 days.

(21) Appl. No.: 15/281,571

(22) Filed: Sep. 30, 2016

(65) Prior Publication Data
US 2017/0100083 A1    Apr. 13, 2017

(30) Foreign Application Priority Data

Oct. 8, 2015 (DE) .................. 10 2015 219 520

(51) Int. Cl.
*A61B 6/00* (2006.01)
*A61B 6/02* (2006.01)
*A61B 6/03* (2006.01)

(52) U.S. Cl.
CPC ........... *A61B 6/027* (2013.01); *A61B 6/032* (2013.01); *A61B 6/4441* (2013.01); *A61B 6/5205* (2013.01)

(58) Field of Classification Search
CPC ............................ A61B 6/032; A61B 6/4441
See application file for complete search history.

(56) References Cited

U.S. PATENT DOCUMENTS

2006/0023830 A1   2/2006  Schomberg
2007/0268994 A1*  11/2007 Chen ................. A61B 6/032
                                                                 378/4

(Continued)

FOREIGN PATENT DOCUMENTS

DE         10147160 C1    4/2003
DE         10211016 A1    9/2003
DE        102009061749 A1  6/2015

OTHER PUBLICATIONS

German Office Action for German Application No. 102015219520.1, dated Jun. 17, 2016, with English Translation.

(Continued)

*Primary Examiner* — Dani Fox
(74) *Attorney, Agent, or Firm* — Lempia Summerfield Katz LLC

(57) ABSTRACT

A tomography system with a beam source and a detector that is adapted to carry out a scan. While the beam source is guided along a circular or helical first trajectory about an orbital axis, a rectangular sensor surface of the detector is guided at a distance from the beam source along a circular or helical second trajectory about the orbital axis. During the scan, a yaw angle between a perpendicular bisector of the sensor surface and the plane of rotation in which the beam source is currently located has a value of greater than 0° and simultaneously smaller than 90°.

20 Claims, 7 Drawing Sheets

(56) References Cited

U.S. PATENT DOCUMENTS

2008/0292046 A1   11/2008  Camus et al.
2016/0171723 A1*  6/2016   Claus .................... A61B 6/032
                                                    382/131

OTHER PUBLICATIONS

Maier, A. el al.: "Discrete Estimation of Data Completeness for 3D Scan Trajectories with Detector Offset", in: https://www5.informatik.uni-erlangen.de/Forschung/Publikationen/2015/Maier15-DEO.pdf, 2015.

Stromer, D. et. al: "Data Completeness Estimation for 3D C-arm Scans with Rotated Detector to enlarge the lateral Field-of-view", in: https://www5.informatik.uni-erlangen.de/Forschung/Publikationen/2016/Stromer16-DCE.pdf, 2016.

* cited by examiner

FIG 12

| Scan Mode | SID [mm] | Detector Rotation | Detector shift [mm] | Coverage [mm] | F-o-V [mm x mm] |
|---|---|---|---|---|---|
| Short Scan | 1200 | no | 0 | 320 | 310 x 240 |
| Short Scan | 1200 | yes | 0 | 384 | 390 x 120 |
| Large Volume Scan | 1200 | no | 310 | 576 | 620 x 240 |
| Large Volume Scan | 1200 | yes | 390 | 672 | 780 x 120 |
| Large Volume Scan | 900 | no | 310 | 704 | 620 x 240 |
| Large Volume Scan | 900 | yes | 390 | 800 | 780 x 120 |
| Large Volume Scan | 900 | yes | 370 | 768 | 740 x 140 |
| Helical Scan | 900 | yes | 390 | 800 | 780 x 290 |
| Helical Scan | 900 | yes | 370 | 768 | 740 x 320 |

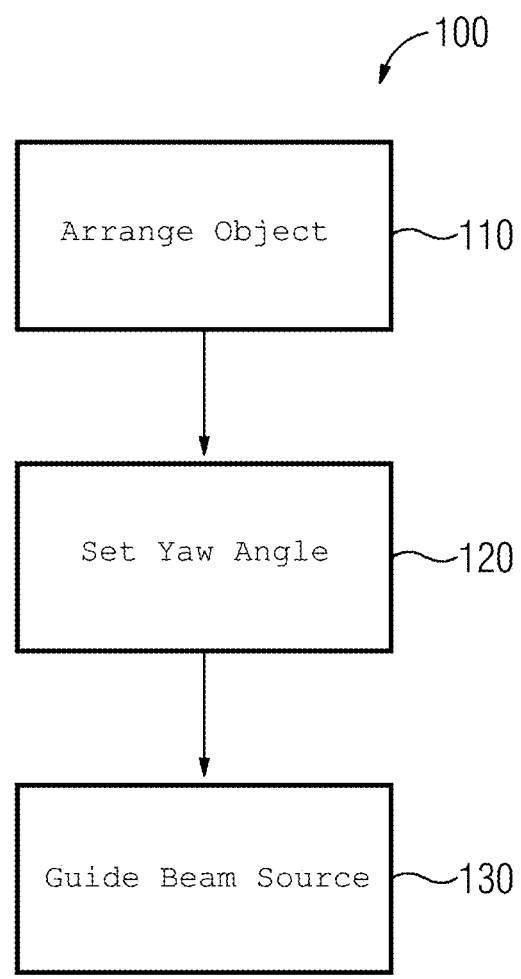

TOMOGRAPHY FOR LARGE VOLUME 3D SCANS

RELATED CASE

This application claims the benefit of DE 102015219520.1, filed on Oct. 8, 2015, which is hereby incorporated by reference in its entirety.

FIELD

The present embodiments relate to a tomography system with a beam source and a detector and corresponding method. The tomography system is adapted to carry out a scan, while the beam source is guided along a circular or helical first trajectory about an orbital axis and while a rectangular sensor surface of the detector is guided at a distance from the beam source along a circular or helical second trajectory about the orbital axis. The first and second trajectories are typically arranged concentrically with respect to one another. The second circular trajectory typically lies in the plane of rotation of the first circular trajectory. In a particularly preferred embodiment, the distance between the beam source and the sensor surface remains constant, while the sensor surface of the detector is guided along the circular or helical second trajectory about the orbital axis. In this case, the second trajectory is also circular when the first trajectory is circular. Moreover, the two trajectories can be identical (albeit temporally offset to one another). The beam source and the detector can be secured to a common mobile carrier, for example their own C-arm or to different mobile carriers, for example each on a robot arm. Optionally, an image intensifier can be connected to the detector. One option independent thereof provides that that the detector is an image intensifier. The tomography system can, for example, be an X-ray tomography system or a fluorescence tomography system.

BACKGROUND

In diagnostics and therapy, increasingly high requirements are placed on the quality of medical equipment. The object thereof is in particular to avoid risks to health and personal injuries due to faulty diagnoses or treatment.

DE 101 47 160 C1 describes a C-arm tomography system with a rectangular detector mounted rotatably by 90° about a connecting axis to the beam source in order, despite the limited size of the detector surface, to ensure that the object to be reconstructed is largely completely covered in the projection exposures in all rotational directions.

SUMMARY AND DETAILED DESCRIPTION

It is an object to provide a tomography system with a C-arm and a method for obtaining projection data with which even larger volume 3D scans can be performed than with the known C-arm tomography system.

According to one embodiment, this object is achieved by a tomography system with a beam source and a detector. The tomography system is adapted to carry out a scan, while the beam source is guided along a circular or helical first trajectory about an orbital axis and while a rectangular sensor surface of the detector is guided at a distance from the beam source along a circular or helical second trajectory about the orbital axis. During the scan, a yaw angle between a perpendicular bisector of the sensor surface and a plane of rotation in which the beam source is currently located has a value of greater than 0° and simultaneously smaller than 90°.

The method according to one embodiment for obtaining projection data includes the following acts. In a first method act, an examination object is arranged between a beam source and a rectangular sensor surface of a detector. In a second method act, a yaw angle between a perpendicular bisector of the sensor surface and a plane of rotation in which the beam source is currently located is set to a value greater than 0° and less than 90° by swiveling the sensor surface about a surface normal of the sensor surface. In a third method act, the beam source is guided along a circular or helical first trajectory about an orbital axis while the sensor surface of the detector is guided at a distance from the beam source along a circular or helical second trajectory about the orbital axis. The beam source is active in at least a plurality of orbital positions in order to X-ray the examination object. The second method act can also be performed before or simultaneously with the first method step.

One concept can be seen as being that the yaw angle between a perpendicular bisector of the sensor surface and a plane of rotation in which the beam source is currently located has a value greater than 0° and less than 90°. This increases a maximally effective length in a direction of rotation of the sensor surface without requiring changes to the other settings and dimensions of the tomography system or the sensor surface.

It is advantageous for the tomography system to be adapted to carry out the scan while a diagonal of the sensor surface extends parallel to the plane of rotation. This arrangement is synonymous with the setting of a yaw angle in which the effective length in the direction of rotation of the sensor surface assumes a maximum value.

It is particularly preferable for the tomography system to be adapted to carry out the scan while the diagonal of the sensor surface lies in the plane of rotation. The efficiency of the image generation is typically greatest when the center point of the sensor surface lies in the radial plane of the first trajectory. If simultaneously a yaw angle is to be set in which the effective length in the direction of rotation of the sensor surface assumes a maximum value, this is synonymous with the diagonal of the sensor surface lying in the plane of rotation.

Irrespective, one expedient development envisages that the tomography system is adapted to carry out the scan while the orbital axis is arranged parallel to the sensor surface. In this alignment of the sensor surface, the beam angle that can be acquired by the sensor surface in a circumferential position is maximal. However, circumstances are also conceivable in which an inclination of the sensor surface with respect to the orbital axis can be advantageous. For example, an inclination of the sensor surface with respect to the orbital axis enables a higher resolving power to be achieved in the orbital axis direction with unchanged sensor technology.

In the plane of rotation, the diameter of the evaluable volume can be increased still further if the tomography system is adapted to carry out the scan while an isocenter is guided along a circular third trajectory. An axis of rotation of the circular third trajectory is fixed during the scan with respect to a reference system of an examination object.

In addition, an extension of the evaluable volume can be increased still further if the tomography system is adapted to carry out the scan while an isocenter is guided along a helical fourth trajectory. An axis of rotation of the helical fourth trajectory is fixed during the scan with respect to a reference system of an examination object.

It is advantageous for the tomography system to be adapted to carry out the scan while the yaw angle is greater than 5° or greater than 10° or greater than 20°. Irrespective thereof, it is advantageous for the tomography system to be adapted to carry out the scan, while the yaw angle is less than 85° or less than 80° or less than 70°.

In a particularly preferred embodiment, the tomography system includes a C-arm that is swivel-mounted in an angular and/or orbital fashion about an orbital axis of the C-arm. The C-arm bears the beam source on a first end of the C-arm and the detector on a second end of the C-arm. The detector with the sensor surface is mounted rotatably about a surface normal of the sensor surface. This enables the diameter of the evaluable volume to be adapted to current applicational requirements by manual or motorized setting of the yaw angle.

BRIEF DESCRIPTION OF THE DRAWINGS

The embodiments are explained in more detail with reference to the attached drawings, which show:

FIG. 12 is a table, according to one embodiment, with a comparison of the settings and the diameters of the evaluable volumes of the suggested scanning methods; and FIG. 13 is a schematic view of the course of a method, according to one embodiment, for obtaining projection data.

DETAILED DESCRIPTION

The following exemplary embodiments described in more detail represent preferred embodiments.

Figure 1:
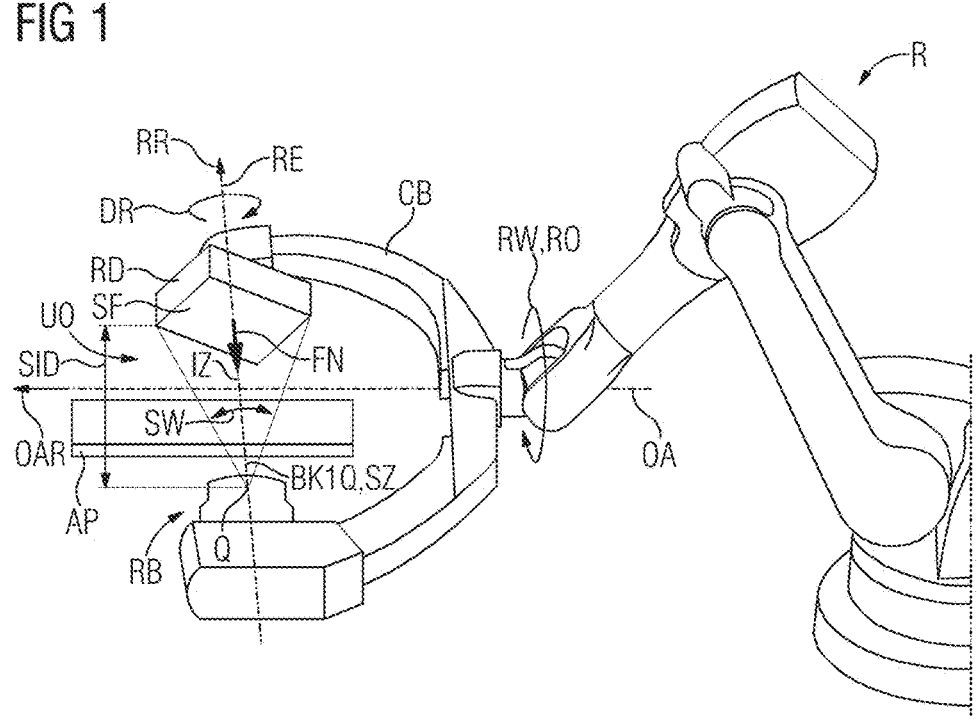
FIG. 1 is a schematic perspective view of a C-arm tomography device with a beam source, a detector, and a patient support, according to one embodiment.

FIG. 1 shows one embodiment of a tomography device R with a C-arm CB, a beam source Q, a detector RD and a patient support AP. The detector RD includes a sensor surface SF.

Two procedures are commonly used in clinical practice in order to perform a 3D-scan by a multi-axis C-arm system R along a circular trajectory BK1. The first procedure is called a short scan, and the second procedure is called a large volume scan.

With the short scan, an angular or orbital rotation RO of the C-arms of 180° plus a beam angle SW is performed about the orbital axis OA in order to obtain the minimal complete dataset for the given geometry. FIG. 1 shows a position of the C-arm CB during an angular rotation RO. During a (not shown in the figures) orbital rotation RO, the C-arm CB is perpendicular to the orbital axis OA.

Figure 2:
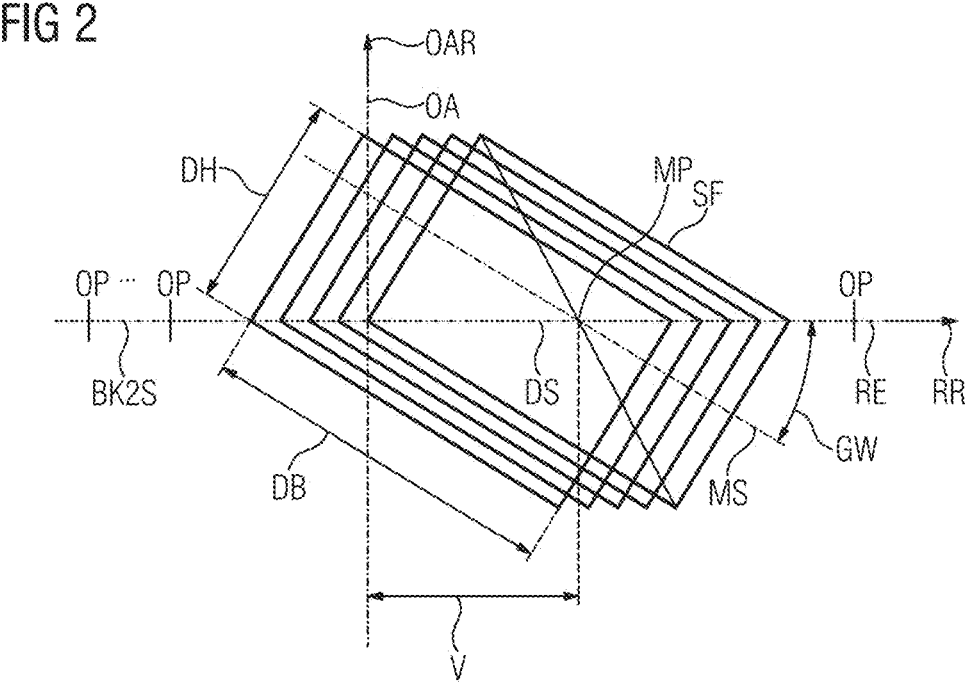
FIG. 2 is a schematic view of an example arrangement of a sensor surface of the detector in FIG. 1.

A large volume scan performs an angular or orbital 360° rotation RO about the orbital axis OA in the direction of rotation RR, wherein a center point MP of the sensor surface SF is shifted with respect to a central beam ZS of the beam bundle RB by a half a detector width DB (see FIG. 2). This increases the diameter DV of the evaluable volume AV in the direction of rotation RR by approximately a factor of 2.

Depending upon the clinical workflow, even with a large volume scan, the diameter DV of the evaluable volume AV is still too small to cover the entire region of interest (e.g., in the case of scans of the liver of a large patient). At the same time, it may be possible to accept a reduction in the extension HV of the evaluable volume AV in the direction of orbital axis OAR (i.e., perpendicular to the direction of rotation RR). Therefore, for such applications, there is a requirement to increase the diameter DV of the evaluable volume AV in the direction of rotation RR.

Current robot C-arm systems R permit the use of a large number of trajectories. The following describes a method with which the lateral coverage for short scans and large volume scans can be enlarged by a rotation DR of the sensor surface SF about a surface normal FN of the sensor surface SF. With this procedure, the extension AF of the field of view F in the direction of rotation RR is no longer limited to the length of the longest side of the sensor surface SF. Instead, it is possible to use the entire length of the diagonal DS of the sensor surface SF. This concept can be combined with existing methods and new trajectories.

In short-scan mode, rotating data acquisition with an angle of rotation RW of 200° (i.e. 180° plus 20° beam angle SW) about the orbital axis OA is performed in order to obtain a minimal complete dataset for the beam geometry. In this case, the sensor surface SF is aligned either in landscape mode or portrait mode. The rotation RR is performed along a circular trajectory BK1 about the isocenter IZ.

The large volume scan covers a complete rotation RR about 360° about the orbital axis OA. The sensor surface SF is shifted in the direction of rotation RR by a half extension AS of the sensor surface SF (e.g., the extension AS of the sensor surface SF is in the direction of rotation RR). This shift V of the sensor surface SF increases the diameter DV of the evaluable volume AV by a factor of 2 compared to the short scan. In this operating mode, the sensor surface SF is in either landscape mode or portrait mode. Instead of shifting the sensor surface SF, in practical implementation, the rotation RR is usually performed about a planetary axis PA, which is guided along a third circular trajectory BK3 about the orbital axis OA during the scan. With a detector size (i.e., size of the sensor surface SF) of 640 mm×480 mm, the shift for a large volume scan without rotation DR of the sensor surface SF is 310 mm, which enlarges the diameter DV of the evaluable volume AV to 620 mm.

Unlike the case with known procedures that use the sensor surface SF in either portrait or in landscape mode, the diameter DV of the evaluable volume AV may be enlarged in that data is acquired with a sensor surface SF that is rotated with respect to the plane of rotation RE in which the beam source Q is currently located about a yaw angle GW. For maximal enlargement of the diameter DV of the evaluable volume AV, the sensor surface SF is rotated until the diagonal DS of the sensor surface SF is in the plane of rotation RE. The optimal yaw angle GW can be calculated with GW=arctan (DB/DH), wherein DB is a width of the sensor surface SF (i.e., detector width) and DH is a height of the sensor surface SF (i.e., detector height).

In short scan mode, a rotation of 200° about the orbital axis OA without detector shift V is performed in order to obtain a minimal complete dataset for cone-beam geometry. In this context, circular trajectories BK1, BK2 with, for example, 200 projection matrices, are used for the beam source Q and sensor surface SF. This produces an average angular increment of 1.0°. With a sensor surface SF of 620 mm×480 mm, the diagonal DS has a length of approximately 784 mm. Compared with the known diameter DV of the evaluable volume AV of 620 mm, an enlargement of the diameter DV of the evaluable volume AV by approximately 26.5% is expected. With the source-to-patient distance, which is half the source-to-sensor distance SID (source-to-image distance), the diameter DV of the evaluable volume AV should be 392 mm instead of 310 mm.

The large volume scan covers a rotation of 360° about the orbital axis OA. The circular trajectory BK1, BK2 for the beam source Q and sensor surface SF then have, for example, 180 projection matrices, which produces an average angular increment of 2.0°. In the case of a large volume scan, the sensor surface SF is shifted in the direction of rotation RR by a half width of the sensor surface SF. This causes the diameter DV of the evaluable volume AV to be increased by a factor of 2 compared to the short scan. With the given dimensions of the sensor surface SF, the shift V is set to 310 mm. If the sensor surface SF is rotated until its diagonal DS lies in the plane of rotation RE, the maximal advisable shift $V_{max}$ of the sensor surface SF is calculated with $$V_{max}=\tfrac{1}{2}\sqrt{(DB^2+DH^2)}.$$

For the above-mentioned dimensions of the sensor surface SF, the maximal advisable shift $V_{max}$ is 392 mm. In order to ensure complete coverage of the data acquisition, the shift V is set to 390 mm. The closer the sensor surface SF is shifted to this limit, the greater the associated reduction in the extension HV of the evaluable volume AV in the orbital axis direction OAR.

FIG. 2 shows different shifts V of the sensor surface SF in the direction of rotation RR. In the case of the maximal shift V, the diameter DV of the evaluable volume AV is increased in the direction of rotation RR to 620 mm or 780 mm. This corresponds to an enlargement of the diameter DV of the evaluable volume AV in the direction of rotation RR by approximately 25.8%.

One drawback of the rotation DR of the sensor surface SF is a loss of information. The further the distance of the information to be depicted from the plane of rotation RE, the greater the loss. To compensate for this, a helical scan can be used in conjunction with the rotated sensor surface SF. One embodiment provides five full rotations, wherein a pitch GH is selected that is as small as possible and as large as necessary. Tests have shown that, with the given detector configuration, a pitch of 9 mm is optimal. In this context, it is assumed that, in this configuration, the diameter DV of the evaluable volume AV remains unchanged in the direction of rotation RR, while an axial length of the evaluable volume AV extends further with every rotation.

Instead of carrying out a full helical scan (which is difficult to implement with current systems), this procedure also enables alternative data acquisition modes to be combined.

A method for arbitrary discretely sampled trajectories can be used to calculate voxel-wise data completeness for the mentioned scans. The method calculates the three-dimensional evaluable volume of Radon plane normals on a unit sphere and intensities between 0 and 1 at each voxel. The result is a three-dimensional image with a predefined image size. To speed up the calculations, the image size can be set to 64×64×64 voxels with a voxel spacing of 16 mm×16 mm×4 mm. For improved depiction, a cut-off value can be set at 0.9. After this, a depiction can be performed by an implemented 'OpenCL Forward Projector' in which the diameter DV of the resultant evaluable volume AV is measured. A voxel spacing of 1 mm×1 mm×1 mm can be set for the projection.

Figure 3:
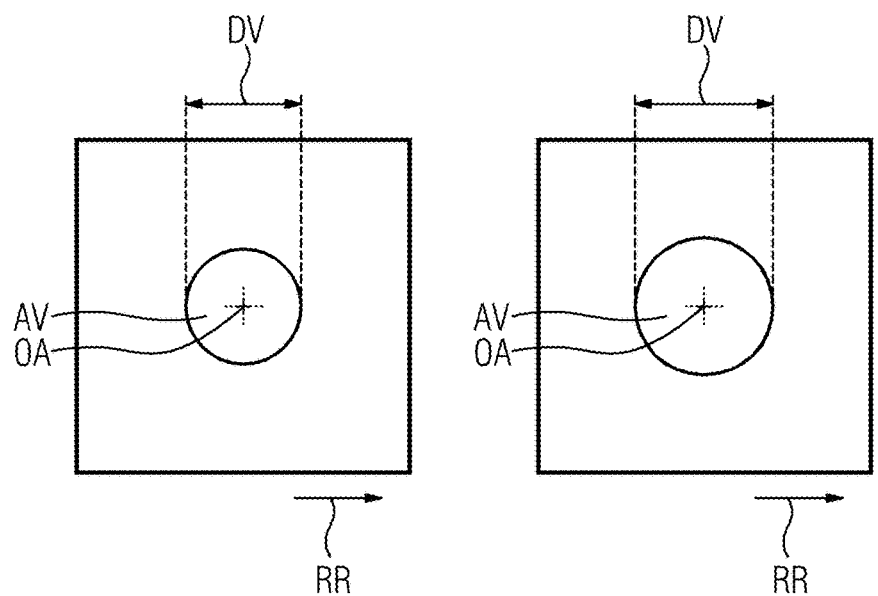
FIG. 3 shows example schematic sectional views of a central disk of the evaluable volume of a short scan with and without rotation of the sensor surface of the detector.

The left-hand part of FIG. 3 is an image of a central disk ZS of the evaluable volume AV for a normal short scan without rotation DR of the sensor surface SF, while the right-hand part of FIG. 3 shows a cut surface of the evaluable volume AV with a rotated sensor surface SF, where the diagonal DS of the sensor surface SF is arranged in the plane of rotation RE. Measuring the diameter DV of the evaluable volume AV reveals an enlargement of the diameter DV of the evaluable volume AV of 4 pixels as a result of the arrangement of the diagonal DS of the sensor surface SF in the plane of rotation RE. A calculation of the diameter DV of the evaluable volume AV in millimeters shows that the expectations are met. For the normal short scan and 384 mm, the arrangement of the diagonal DS of the sensor surface SF in the plane of rotation RE and the predefined voxel spacing of 16 mm achieves a diameter DV of the completely evaluable volume AV of 320 mm. The evaluable volume AV then has a diameter DV which is 64 mm larger than without rotation DR of the sensor surface SF, which means that the arrangement of the diagonal DS of the sensor surface SF in the plane of rotation increases the diameter DV of the evaluable volume AV by 20.0%.

Figure 4:
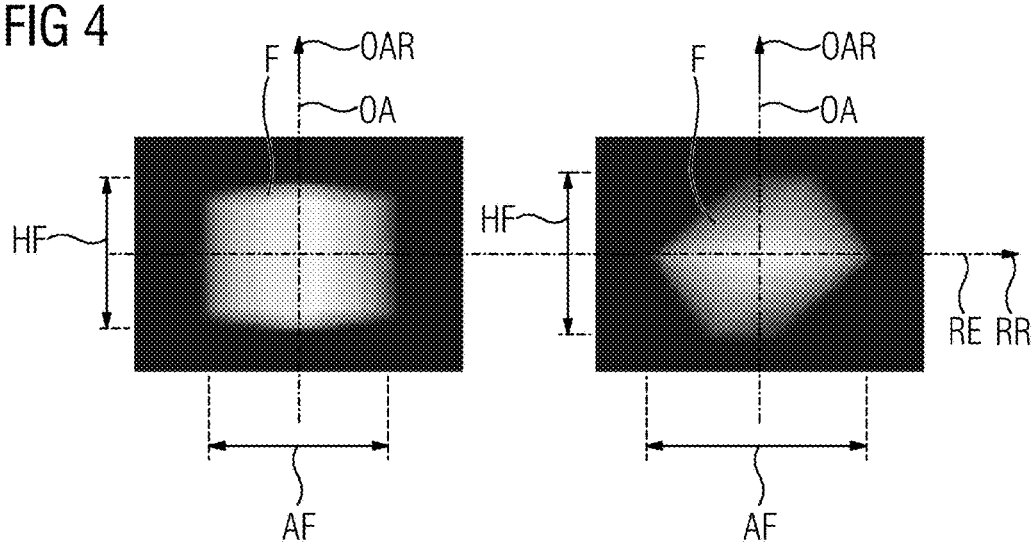
FIG. 4 shows schematic depictions of the evaluable volumes for the settings in FIG. 3, wherein the brightness of the individual pixels in the depictions is a measure of the size of the cut length of the solid angle belonging to the respective pixel.

A reconstruction of the three-dimensional images in FIG. 3 results in a field of view F. The left-hand part of FIG. 4 shows a field of view F of the short scan with a non-rotated sensor surface SF. The right-hand part of FIG. 4 shows a field of view F of the short scan with a rotated sensor surface SF. The (maximal) extension AF of the field of view F of a normal short scan reaches 310 mm in the direction of rotation RR, while the extension AF of the field of view F of the modified scan reaches 390 mm in the direction of rotation RR. This produces an overall difference of 80 mm in the direction of rotation RR. The arrangement of the diagonal DS of the sensor surface SF in the plane of rotation RE produces an enlargement of the extension AF of the field of view F of approximately 25.8% in the direction of rotation RR and matches the expected values exactly. However, the field of view F of the reconstructed image is no longer rectangular—it is now hexagonal.

Figure 5:
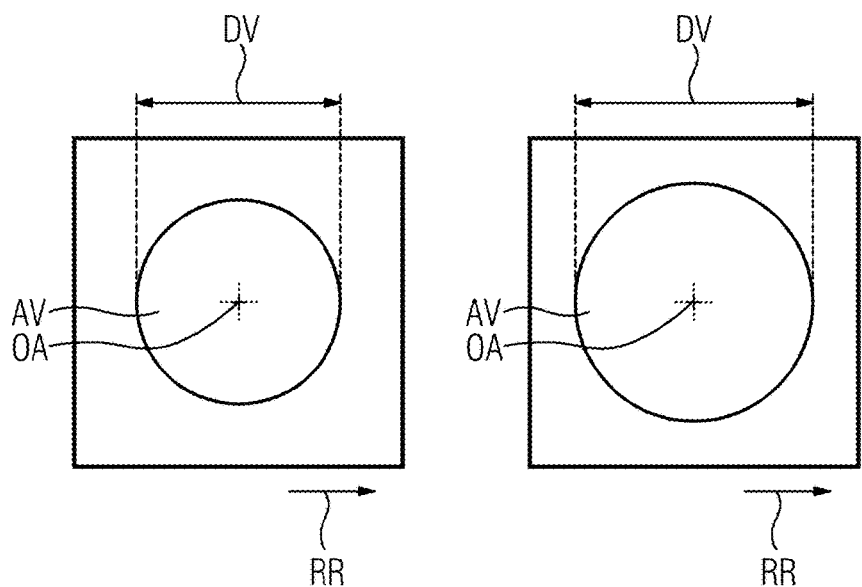
FIG. 5 shows example schematic sectional views of a central disk of the evaluable volume of a large volume scan without rotation of the sensor surface of the detector with a detector shift of 310 mm (left-hand figure) and with a rotated sensor surface of the detector with a detector shift of 390 mm (right-hand figure)

FIG. 5 shows sectional images of the evaluable volume AV that are calculated for two large volume scans. The left-hand part of FIG. 5 is a sectional view of a central disk ZS of the evaluable volume AV for a large volume scan without rotation DR of the sensor surface SF, but with a shift V of the sensor surface SF by a half detector width (310 mm). The right-hand part of FIG. 5 shows a sectional view of a central disk ZS of the evaluable volume AV for a large volume scan with a shift V of the sensor surface SF by half the length of the diagonal DS of the sensor surface SF (390 mm), wherein the diagonal DS of the sensor surface SF is arranged in the plane of rotation RE. The calculated maximal advisable detector shift V is 390 mm. The arrangement of the diagonal DS of the sensor surface SF in the direction of rotation RR and the shift V of the sensor surface SF in the direction of rotation RR increases the diameter DV of the evaluable volume AV by 96 mm in the direction of rotation RR. The diameter DV of the evaluable volume AV is increased by 16.7% from 576 mm to 672 mm.

Figure 6:
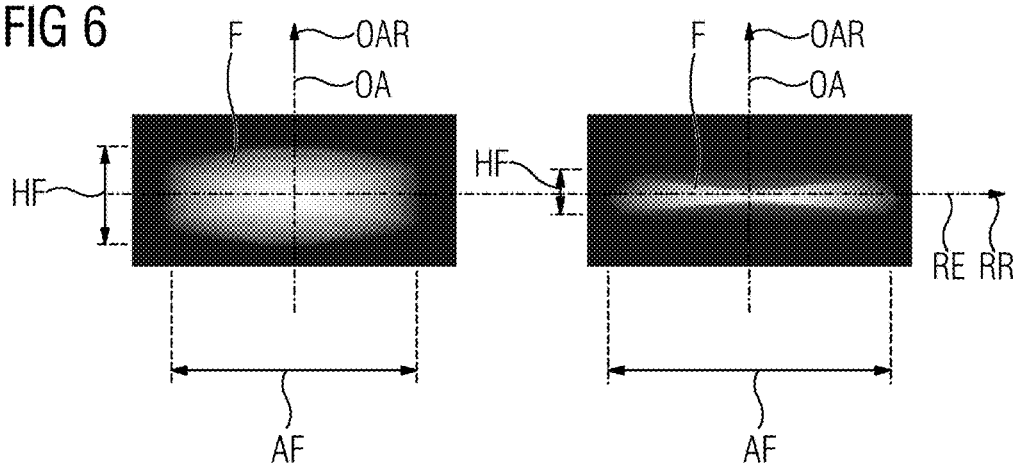
FIG. 6 shows schematic depictions of the evaluable volumes for the settings in FIG. 5, wherein the brightness of the individual pixels in the depictions is a measure of the size of the cut length of the solid angle belonging to the respective pixel.

Following the reconstruction of the three-dimensional images, the fields of view F shown in FIG. 6 are obtained. The left-hand part of FIG. 6 depicts the field of view F of the normal large volume scan with a shift V of the sensor surface SF of 310 mm. The right-hand part of FIG. 6 shows the field of view F for a large volume scan with a shift V of the sensor surface SF by half the length of the diagonal DS of the sensor surface SF (390 mm), wherein the diagonal DS of the sensor surface SF is arranged in the plane of rotation RE. The extension AF of the field of view F in the direction of rotation RR is 620 mm for the normal scan. The extension AF of the field of view F with the diagonal DS arranged in the plane of rotation RE reaches 780 mm. This results in an increase of 25.8% and 160 mm, which also matches the expected values. The extension HF of the field of view F is impaired in the orbital axis direction OAR. The extension HF of the field of view F in the orbital axis direction OAR is very small and not covered uniformly. The extension HF of the field of view F in the orbital axis direction OAR has been halved from 240 mm to 120 mm.

Figure 7:
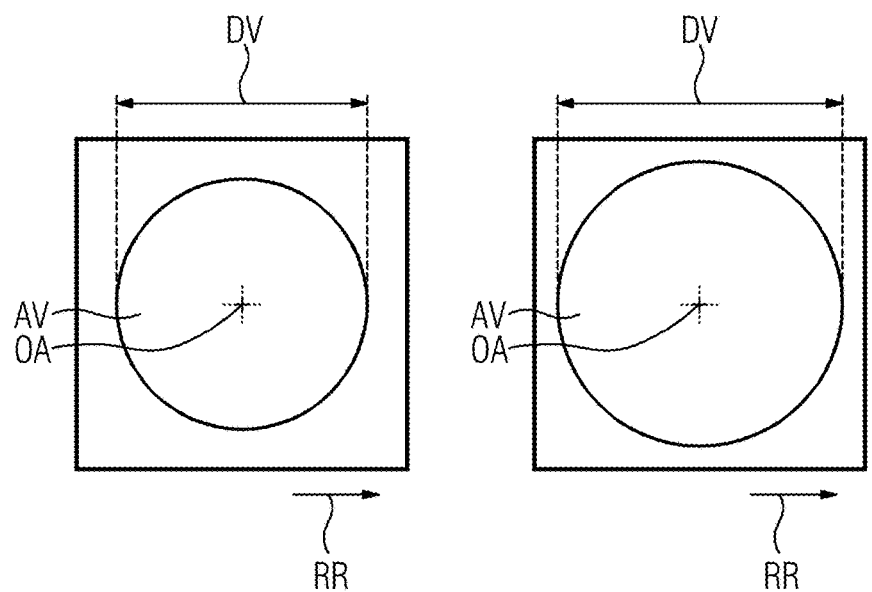
FIG. 7 shows example schematic sectional views of a central disk of a large volume scan for a source-to-sensor distance of 900 mm without rotation of the detector with a detector shift of 310 mm (left-hand figure) and with a rotated detector with a detector shift of 390 mm (right-hand figure)

In order to achieve a still larger diameter DV of the evaluable volume AV, the source-to-sensor distance SID is reduced to 900 mm. A comparison of the diameter DV of the evaluable volume AV of the operation with a sensor surface SF that is rotated and simultaneously shifted by 390 mm (right-hand part of FIG. 7) with the large volume scan (left-hand part of FIG. 7) with a sensor surface SF that is not rotated, but shifted by 390 mm produces the result that the arrangement of the diagonal DS of the sensor surface SF in the plane of rotation RE improves the diameter DV of the evaluable volume AV in the direction of rotation RR by 13.6% from 704 mm to 800 mm.

Figure 8:
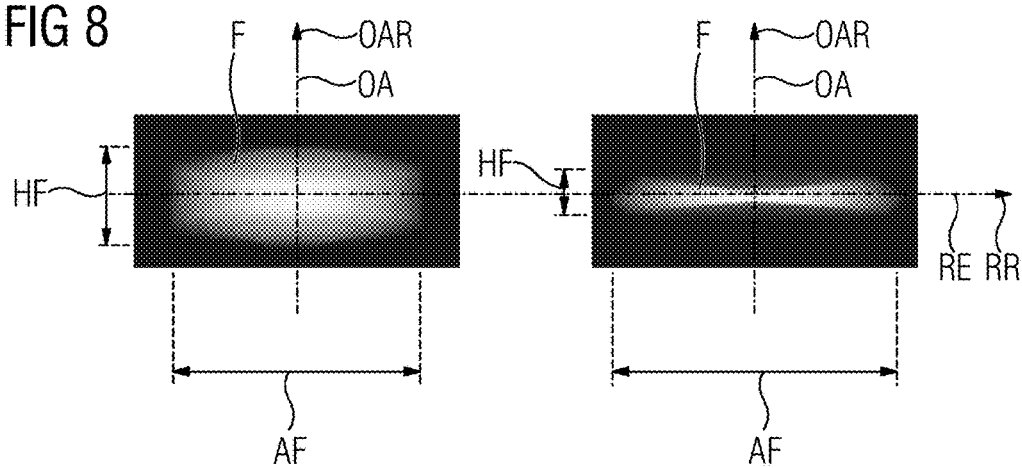
FIG. 8 shows schematic depictions of the evaluable volumes with the settings in FIG. 7, wherein the brightness of the individual pixels in the depictions is a measure of the size of the cut length of the solid angle belonging to the respective pixel.

The fields of view F after reconstruction are shown in FIG. 8. The extension AF of the field of view F of the large volume scan with the diagonal DS of the sensor surface SF arranged in the plane of rotation RE is 620 mm in the direction of rotation RR. For the large volume scan with the diagonal DS of the sensor surface SF arranged in the plane of rotation RE, the extension AF of the field of view F in the direction of rotation RR is 780 mm so that, with the diagonal DS of the sensor surface SF arranged in the plane of rotation RE, a maximal enlargement of the extension of the field of view F of overall 60 mm or 25.8% is achieved in the direction of rotation RR. The extension HF of the new field of view F in the orbital axis direction OAR is still 120 mm, which means that a loss of 50% of field of view extension HF in the orbital axis direction OAR has to be accepted.

The trade-off between the loss of extension HF of the field of view F in the orbital axis direction OAR and the gain of extension of the field of view F in the direction of rotation RR is also investigated and then the shift V of the sensor surface SF in the direction of rotation R is reduced to 370 mm. This adaptation should produce an extension HF of the field of view F in the orbital axis direction OAR of 740 mm. The calculation results in the enlargement of the diameter DV of the evaluable volume AV in the direction of rotation RR to 768 mm, which still represents a gain of 9.1%.

Figure 9:
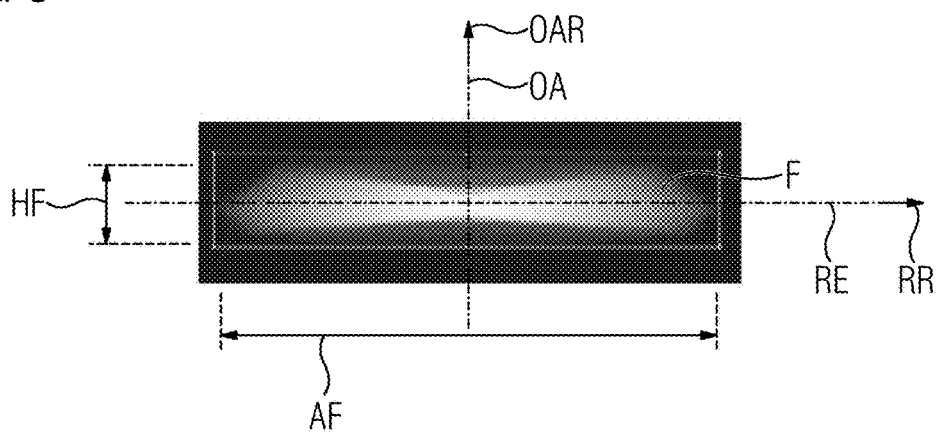
FIG. 9 is an example schematic depiction of the evaluable volume for a large volume scan with a rotated detector, a source-to-sensor distance of 900 mm and a detector shift of 370 mm, wherein the brightness of the individual pixels in the depiction is a measure of the size of the cut length of the solid angle belonging to the respective pixel.

To this end, FIG. 9 shows the fields of view F of the reconstruction of the image of the evaluable volume AV. The gray outline identifies limits GF of the field of view F, which are obtained with the set shift V of the sensor surface SF. The result is a field of view F with an extension AF in the direction of rotation RR of 740 mm and an extension HF in the orbital axis direction OAR of 140 mm. The extension HF of the field of view F in the orbital axis direction OAR is again increased by 20 mm. Compared with a normal large volume scan, this adaptation in the direction of rotation RR provides a further improvement by 19.4%, which is associated with a loss in the orbital axis direction OAR of only 41.7%.

In a further test, helical trajectories BK1, BK2 are used instead of circular trajectories for the beam source Q and sensor surface SF in order to obtain a greater extension HV of the evaluable volume AV in the orbital axis direction OAR. The dimensions DV, HV of the evaluable volume AV remain the same for each rotation. The extension HV of the evaluable volume AV is multiplied with the number of rotations.

Figure 10:
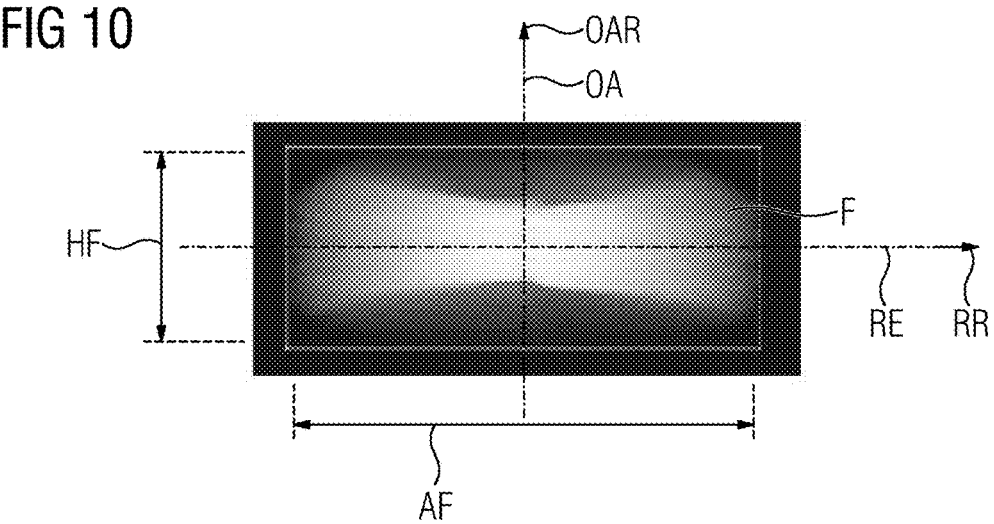
FIG. 10 is an example schematic depiction of the evaluable volume for a helical scan with a rotated detector and a detector shift of 390 mm, wherein the brightness of the individual pixels in the depiction is a measure of the size of the cut length of the solid angle belonging to the respective pixel.

FIG. 10 shows the resulting fields of view F of the reconstruction of the evaluable volume AV. As expected, the extension AF of the field of view F in the direction of rotation RR is still 780 mm. The measured extension HF of the field of view F in the orbital axis direction OAR is 290 mm. Hence, the five rotations of the helical scan expand the extension HF of the field of view F in the orbital axis direction OAR by a factor of approximately 240% compared to the circular scan.

Figure 11:
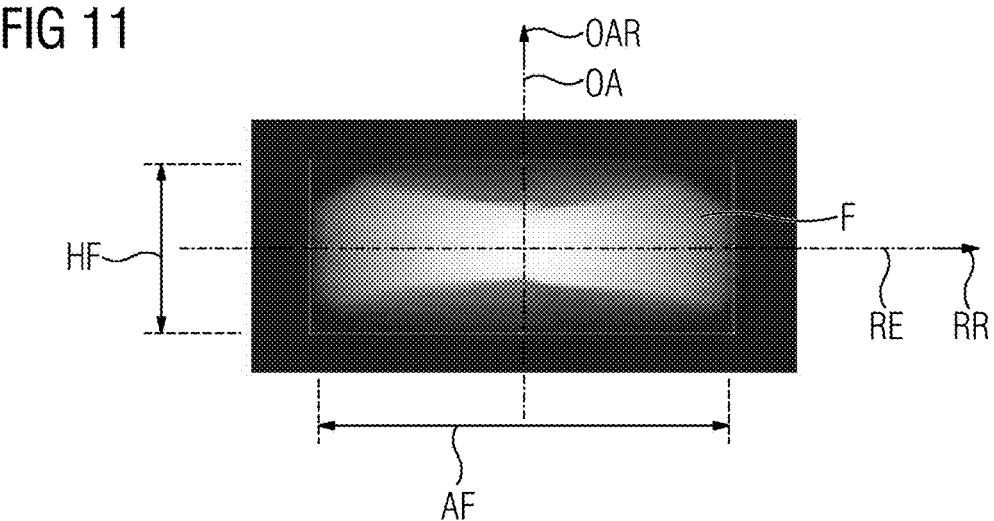
FIG. 11 is an example a schematic depiction of the evaluable volume for a helical scan with a rotated detector and a detector shift of 370 mm, wherein the brightness of the individual pixels in the depiction is a measure of the size of the cut length of the solid angle belonging to the respective pixel.

It is also possible for the shift V of the sensor surface SF to be reduced again by 20 mm to 370 mm. FIG. 11 shows the results. Compared with the helical scan with the maximal shift V, the extension AF of the field of view F is reduced in the direction of rotation RR by 40 mm to 740 mm, but an enlargement of the field of view F in the orbital axis direction OAR of up to 320 mm is achieved. This is 228% more than with a circular scan or 33.33% more than with a large volume scan without rotation DR of the sensor surface SF.

A comparison of the results shows that a diameter DV of the evaluable volume AV can be increased in the direction of rotation RR while entailing a loss in the extension HV of the evaluable volume in the orbital axis direction OAR. The new field of view F is then not rectangular but hexagonal. As a result, information is lost at the edges of a volume to be examined in the orbital axis direction OAR if the volume to be examined has the same extension in the orbital axis direction OAR as in the direction of rotation RR. If it is known that there is more interest in depicting the volume to be examined in the direction of rotation RR than in the orbital axis direction OAR, a rotation DR of the sensor surface SF can be used in order to increase an extension of the field of view F in the direction of rotation RR. A trade-off between the enlargement of the field of view F in the direction of rotation RR and the reduction of the field of view F in the orbital axis direction OAR can be achieved by setting the detector shift V or the rotation DR to an interim value. If, despite the rotation DR of the sensor surface SF, a greater extension HV of the evaluable volume AV in the orbital axis direction OAR is desired, this can be achieved with a helical scan.

The effect that this scanning geometry creates a set of redundantly samples partial volumes can be reduced by limiting a beam angle SW of the beam RS in the orbital axis direction OAR by collimation. This ultimately produces a scanning geometry that is very similar to a diagnostic CT scanner with a long, but very narrow sensor surface SF.

The table depicted in FIG. 12 contains a comparison of the results for an isocenter IZ at 600 mm. In the table, F-o-V designates the field of view F obtained from the reconstruction. The values for the helical scan relate to scans with five rotations.

Under otherwise identical conditions, with a source-to-sensor distance SID of 1200 mm and a rotation DR of the sensor diagonal DS into the rotation plane RE, for the scan modes 'short scan' and 'large volume scan', an extension AF of the field of view F is increased in the direction of rotation RR by 25.8% and simultaneously an extension HF of the field of view F is reduced in the orbital axis direction OAR by 50%. An additional reduction of the source-to-sensor distance SID to 900 mm can increase an extension AF of the field of view F in the direction of rotation RR by a further 128 mm (i.e., by a further 13.6%).

In large volume scan mode with a detector diagonal DS in the plane of rotation RE, a reduction in the shift V of the sensor surface SF by 20 mm results in a reduced axial loss of only 41.7% instead of 50%. The enlargement of the diameter DV of the evaluable volume AV is then 9.1%. The enlargement of the extension AF of the field of view F in the direction of rotation RR is 19.4%. To enlarge the field of view F in the orbital axis direction OAR, helical trajectories BK1, BK2 can be used for the beam source Q and sensor surface SF, with which the extension AF of the field of view F in the direction of rotation RR is the same as with a circular trajectory BK1, but the extension HF of the field of view F in the orbital axis direction OAR is proportional to the number of rotations. The maximal possible shift V of 390 mm and five rotations expands the field of view to 290 mm. A detector shift trade-off of minus 20 mm can achieve an extension AF of the field of view F in the direction of rotation RR of 320 mm, which is 33.3% more than that with a large volume scan.

Therefore, in combination with the mentioned scan modes, a rotation DR of the sensor surface SF can produce more accurate results than known scan methods. This in particular applies to imaging examinations of long, slender volumes, such as for imaging a patient.

The method 100 depicted in FIG. 13 for obtaining projection data comprises the following method acts. In a first method act 110, an examination object UO is arranged between a beam source Q and a rectangular sensor surface SF of a detector RD. In a second method act 120, a yaw angle GW is set between a perpendicular bisector MS of the sensor surface SF and a plane of rotation RE in which the beam source Q is currently located by swiveling DR the sensor surface SF about a surface normal FN of the sensor surface SF to a value greater than 0° and less than 90°. In a third method act 130, the beam source Q is guided along a circular or helical first trajectory BK1Q about an orbital axis OA, while the sensor surface SF of the detector RD is guided along a circular or helical second trajectory BK2S about the orbital axis OA. The beam source Q is active in at least a plurality of orbital positions OP in order to X-ray the examination object UO. The second method act 120 can also be performed before or simultaneously with the first method act 110. In a particularly preferred embodiment, a distance SID between the beam source Q and the sensor surface SF is constant, while the sensor surface SF of the detector RD is guided along the circular or helical second trajectory BK2S about the orbital axis OA.

The invention relates to a tomography system R with a beam source Q and a detector RD, which is adapted to carry out a scan, while the beam source Q is guided along a circular or helical first trajectory BK1Q about an orbital axis OA. In synchronism therewith, a rectangular sensor surface SF of the detector RD is guided at a distance SID to the beam source Q along a circular or helical second trajectory BK2S about the orbital axis OA. During the scan, a yaw angle GW between a perpendicular bisector MS of the sensor surface SF and the plane of rotation RE in which the beam source Q is currently located has a value greater than 0° and simultaneously smaller than 90°.

It is intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

The invention claimed is:

1. A tomography system for performing a scan, the tomography system comprising:
   a beam source; and
   a detector with a rectangular sensor surface;
   wherein, during the scan, the beam source is guided along a circular or helical first trajectory about an orbital axis, while the rectangular sensor surface of the detector is guided at a distance from the beam source along a circular or helical second trajectory about the orbital axis (OA); and,
   wherein, during the scan, the rectangular sensor surface is positioned with a perpendicular bisector of the rectangular sensor surface at a yaw angle between the perpendicular bisector of the sensor surface and the orbital axis in a plane of the rectangular sensor surface having a value of greater than 0° and smaller than 90°.

2. The tomography system as claimed in claim 1, wherein, during the scan, a diagonal of the sensor surface extends parallel to a plane of rotation in which the beam source is currently located.

3. The tomography system as claimed in claim 2, wherein, during the scan, the diagonal of the sensor surface lies in the plane of rotation.

4. The tomography system as claimed in claim 1, wherein, during the scan, the orbital axis is arranged parallel to the sensor surface.

5. The tomography system as claimed in claim 1, wherein, during the scan, an isocenter is guided along a circular third trajectory, wherein an axis of rotation of the circular third trajectory is fixed during the scan with respect to a reference system of an examination object.

6. The tomography system as claimed in claim 5, wherein, during the scan, an isocenter is guided along a helical fourth trajectory, wherein an axis of rotation of the helical fourth trajectory during the scan is fixed with respect to a reference system of an examination object.

7. The tomography system as claimed in claim 1, wherein, during the scan, the yaw angle is greater than 5° and less than 85°.

8. The tomography system as claimed in claim 1, wherein, during the scan, the yaw angle is greater than 10° and less than 80°.

9. The tomography system as claimed in claim 1, wherein, during the scan, the yaw angle is greater than 20° and less than 70°.

10. The tomography system as claimed in claim 1, further comprising:
a C-arm that is swivel-mounted in an angular, orbital or orbital and angular fashion about the orbital axis and bears the beam source on a first end and the detector on a second end;
wherein the detector with the sensor surface is mounted rotatably about a surface normal of the sensor surface.

11. The tomography system as claimed in claim 3, wherein, during the scan, the orbital axis is arranged parallel to the sensor surface.

12. The tomography system as claimed in claim 11, wherein, during the scan, an isocenter is guided along a circular third trajectory, wherein an axis of rotation of the circular third trajectory is fixed during the scan with respect to a reference system of an examination object.

13. The tomography system as claimed in claim 12, wherein, during the scan, the yaw angle is greater than 5° and less than 85°.

14. The tomography system as claimed in claim 12, wherein, during the scan, the yaw angle is greater than 10° and less than 80°.

15. The tomography system as claimed in claim 12, wherein, during the scan, the yaw angle is greater than 20° and less than 70°.

16. The tomography system as claimed in claim 12, further comprising:
a C-arm that is swivel-mounted in an angular, orbital or orbital and angular fashion about the orbital axis and bears the beam source on a first end and the detector on a second end;
wherein the detector with the sensor surface is mounted rotatably about a surface normal of the sensor surface.

17. A method for obtaining projection data, the method comprising:
arranging an examination object between a beam source and a rectangular sensor surface of a detector;
setting a yaw angle between a perpendicular bisector of the sensor surface and an axis of rotation in which the beam source is currently located by a swivel of the sensor surface about a surface normal of the sensor surface to a value, the value greater than 0° and less than 90°; and
guiding the beam source along a circular or helical first trajectory about an orbital axis, while the sensor surface of the detector is guided at a distance from the beam source along a circular or helical second trajectory about the orbital axis,
wherein the beam source is active in at least a plurality of orbital positions in order to X-ray the examination object.

18. The method as claimed in claim 17, wherein setting comprises setting a diagonal of the sensor surface to extend parallel to the plane of rotation and to lay in the plane of rotation.

19. The method as claimed in claim 17, wherein guiding comprise guiding an isocenter along a circular third trajectory, wherein an axis of rotation of the circular third trajectory is fixed during the scan with respect to a reference system of an examination object.

20. The method as claimed in claim 17, wherein in setting comprises setting the value to be greater than 20° and less than 70°.

* * * * *